(12) United States Patent
Keravel et al.

(10) Patent No.: US 7,107,104 B2
(45) Date of Patent: Sep. 12, 2006

(54) IMPLANTABLE CORTICAL NEURAL LEAD AND METHOD

(75) Inventors: Yves Keravel, Saint-Maur-des-Fosses (FR); Jean Paul N'Guyen, La Varenne St. Hilaire (FR); Paulus Van Venrooij, Hoensbroek (NL); Frans L. H. Gielen, Eckelrade (NL); Thomas E. Cross, Jr., St. Francis, MN (US)

(73) Assignee: Medtronic, Inc., Minneapolis, MN (US)

( * ) Notice: Subject to any disclaimer, the term of this patent is extended or adjusted under 35 U.S.C. 154(b) by 502 days.

(21) Appl. No.: 10/448,645

(22) Filed: May 30, 2003

(65) Prior Publication Data

US 2004/0243205 A1    Dec. 2, 2004

(51) Int. Cl.
*A61N 1/05*  (2006.01)
(52) U.S. Cl. ............... 607/116; 600/544; 600/545; 600/377; 600/378; 607/45; 607/46; 607/118; 607/152; 607/149
(58) Field of Classification Search ............... 607/116, 607/117, 152, 149, 118, 45, 46; 600/544, 600/545, 377, 378; 439/449, 456
See application file for complete search history.

(56) References Cited

U.S. PATENT DOCUMENTS

| | | | |
|---|---|---|---|
| 3,724,467 A * | 4/1973 | Avery et al. ............... 607/117 |
| 4,092,985 A * | 6/1978 | Kaufman ..................... 606/32 |
| 4,603,696 A | 8/1986 | Cross, Jr. et al. |
| 4,869,255 A | 9/1989 | Putz |
| 4,907,597 A | 3/1990 | Chamoun |
| 5,044,368 A | 9/1991 | Putz |
| 5,097,835 A | 3/1992 | Putz |
| 5,136,687 A | 8/1992 | Edelman et al. |
| 5,143,081 A | 9/1992 | Young et al. |
| 5,269,303 A | 12/1993 | Wernicke et al. |
| 5,417,719 A | 5/1995 | Hull et al. |
| 5,484,445 A * | 1/1996 | Knuth ......................... 606/129 |
| 5,702,429 A | 12/1997 | King |
| 5,711,316 A | 1/1998 | Elsberry et al. |
| 5,713,922 A | 2/1998 | King |
| 5,865,842 A * | 2/1999 | Knuth et al. ................ 607/116 |
| 5,938,688 A | 8/1999 | Schiff |
| 6,006,124 A * | 12/1999 | Fischell et al. ............. 600/378 |
| 6,038,480 A | 3/2000 | Hrdlicka et al. |

(Continued)

FOREIGN PATENT DOCUMENTS

EP    0 998 958 A2    5/2000

(Continued)

OTHER PUBLICATIONS

Tsubokawa T. et al., "Chronic Motor Cortex Stimulation for the Treatment of Central Pain," *Acta Neurochirurgica Suppl.* 52: 137-139, 1991.

(Continued)

*Primary Examiner*—Robert E Pezzuto
*Assistant Examiner*—Deborah Malamud
(74) *Attorney, Agent, or Firm*—John W. Albrecht

(57) ABSTRACT

A neural lead and method of treating neurological disorders by stimulation of the cerebral cortex of the brain is provided. The lead is designed for reduction of strain between the lead body and the lead paddle caused by the position of the lead body above the cranium and the lead paddle beneath the cranium. The lead is also designed to include a two dimensional chronic electrode array for better stimulation coverage of the target area of the cerebral cortex. A method of treating a neurological disorder by stimulating the cerebral cortex is also presented.

14 Claims, 7 Drawing Sheets

U.S. PATENT DOCUMENTS

| | | | |
|---|---|---|---|
| 6,058,331 A | 5/2000 | King | |
| 6,066,163 A | 5/2000 | John | |
| 6,091,979 A | 7/2000 | Madsen | |
| 6,094,598 A | 7/2000 | Elsberry et al. | |
| 6,096,510 A | 8/2000 | Hochman | |
| 6,128,537 A | 10/2000 | Rise | |
| 6,171,239 B1 | 1/2001 | Humphrey | |
| 6,227,203 B1 | 5/2001 | Rise et al. | |
| 6,253,109 B1 | 6/2001 | Gielen | |
| 6,263,237 B1 | 7/2001 | Rise | |
| 6,319,241 B1 | 11/2001 | King et al. | |
| 6,356,784 B1 | 3/2002 | Lozano et al. | |
| 6,356,788 B1 | 3/2002 | Boveja | |
| 6,366,813 B1 | 4/2002 | DiLorenzo | |
| 6,463,328 B1 | 10/2002 | John | |
| 6,473,653 B1 | 10/2002 | Schall Horn et al. | |
| 6,484,059 B1 | 11/2002 | Gielen | |
| 6,517,361 B1* | 2/2003 | Yatskov et al. | 439/67 |
| 6,539,263 B1 | 3/2003 | Schiff et al. | |
| 6,573,063 B1 | 6/2003 | Hochman | |
| 2001/0003799 A1 | 6/2001 | Baveja | |
| 2001/0008972 A1 | 7/2001 | Gielen | |
| 2001/0029391 A1 | 10/2001 | Gluckman et al. | |
| 2002/0016638 A1 | 2/2002 | Mitra et al. | |
| 2002/0035377 A1* | 3/2002 | Bardy et al. | 607/4 |
| 2002/0087201 A1 | 7/2002 | Firlick et al. | |
| 2002/0091419 A1 | 7/2002 | Firlik et al. | |
| 2002/0116030 A1 | 8/2002 | Rezai | |
| 2002/0128700 A1* | 9/2002 | Cross, Jr. | 607/117 |
| 2002/0151939 A1 | 10/2002 | Rezai | |
| 2002/0177882 A1 | 11/2002 | DiLorenzo | |
| 2002/0183817 A1 | 12/2002 | Van Venrooij et al. | |
| 2003/0050569 A1* | 3/2003 | Shenoy et al. | 600/544 |
| 2003/0074032 A1 | 4/2003 | Gliner | |
| 2003/0078522 A1 | 4/2003 | Mitra et al. | |
| 2003/0088274 A1 | 5/2003 | Gliner et al. | |
| 2003/0097159 A1 | 5/2003 | Schiff et al. | |
| 2003/0097161 A1 | 5/2003 | Firlik et al. | |
| 2003/0100931 A1 | 5/2003 | Mullett | |
| 2003/0125786 A1 | 7/2003 | Gliner et al. | |
| 2003/0130706 A1 | 7/2003 | Sheffield | |
| 2003/0149457 A1 | 8/2003 | Tcheng et al. | |
| 2003/0204228 A1* | 10/2003 | Cross et al. | 607/116 |
| 2005/0131506 A1* | 6/2005 | Rezai et al. | 607/117 |

FOREIGN PATENT DOCUMENTS

| | | |
|---|---|---|
| WO | WO 97/39797 A1 | 10/1997 |
| WO | WO 99/20342 A1 | 4/1999 |
| WO | WO 00/07494 A2 | 2/2000 |
| WO | WO 00/09008 A1 | 2/2000 |
| WO | WO 00/76580 A1 | 12/2000 |
| WO | WO 01/37717 A2 | 5/2001 |
| WO | WO 01/41867 A1 | 6/2001 |
| WO | WO 02/45795 A2 | 6/2002 |
| WO | WO 03/066154 A2 | 8/2002 |
| WO | WO 02/072194 A2 | 9/2002 |
| WO | WO 03/026738 A1 | 4/2003 |
| WO | WO 03/026739 A2 | 4/2003 |
| WO | WO 03/035163 A2 | 5/2003 |
| WO | WO 03/041559 A2 | 5/2003 |
| WO | WO 03/055556 A1 | 7/2003 |
| WO | WO 03/063949 A2 | 8/2003 |
| WO | WO 03/066157 A2 | 8/2003 |
| WO | WO 03/066162 A2 | 8/2003 |
| WO | WO 03/082402 A2 | 10/2003 |
| WO | WO 04/052448 A1 | 6/2004 |

OTHER PUBLICATIONS

Nguyen JP et al., "Treatment of Deafferentation Pain by Chronic Stimulation of the Motor Cortex: Report of a Series of 20 Cases," *Acta Neurochirurgica Suppl.* 68: 54-60, 1997.

Katayama Y. et al., "Poststroke Pain Control by Chronic Motor Cortex Stimulation: Neurological Characteristics Predicting a Favorable Response," *J Neurosung* 89: 585-591, 1998.

Hosobuchi Y. et al., "Motor Cortex Stimulation for Control of Central Deafferentation Pain," *Electrical and Magnetic Stimulation of the Brain and Spinal Cord*, Raven Press, 1993.

Mayerson BA et al., "Motor Cortex Stimulation as Treatment of Trigeminal Neuropathic Pain," *Acta Neurochir Suppl.* 58: 150-153, 1993.

Canavero S. et al., "Cortical Stimulation for Central Pain," *J Neurosurg* 83: 1117, 1995.

Herregodts P. et al, "Cortical Stimulation for Central Neuropathic Pain: 3-D Surface MRI for Easy Determination of the Motor Cortex," *ActaNeurochir Suppl.* 64: 132-135, 1995.

Peyron R. et al, "Electrical Stimulation of Precentral Cortical Area in the Treatment of Central pain: Electrophysiological and PET Study," *Pain* 62: 275-286, 1995.

Ebel H. et al., "Chronic Precentral Stimulation in Trigeminal Neuropathic Pain," *Acta Neurochir* 138: 1300-1306, 1996.

Yamamoto et al., "Pharmacological Classification of Central Post-Stroke Pain: Comparison with the Results of Chronic Motor Cortex Stimulation Therapy," *Pain* 72: 5-12, 1997.

Nguyen JP. et al., "Improvement of Action Tremor by Chronic Cortical Stimulation," *Movement Disorders* 13: 84-88, 1998.

Nguyen JP. et al., "Chronic Motor Cortex Stimulation in the Treatment of Central and Neuropathic Pain. Correlations Between Clinical, Electrophysiological and Anatomical Data," *Pain* 82: 245-251, 1999.

Mertens P. et al., "Precentral Cortex Stimulation for the Treatment of Central Neuropathic Pain," *Stereoact Funct Neurosurg* 73: 122-125, 1999.

Roux FE. et al., "Chronic Motor Cortex Stimulation for Phantom Limb Pain: A Functional Magnetic Resonance Imaging Study: Technical Case Report," *Neurosurgery* 48: 681-688, 2001.

Tsubokawa T. et al., "Chronic Motor Cortex Stimulation in Patients with Thalamic Pain," *J Neurosurg* 78: 393-401, 1993.

Franzini A. et al., "Reversal of Thalamic Hand Syndrome by Long-Term Motor Cortex Stimulation," *J Neurosurg* 93: 873-875, 2000.

Canavero S. et al., "Painful Supernumerary phantom Arm Following Motor Cortex Stimulation for Central Post-Stroke Pain," *J Neurosurg* 91: 121-123, 1999.

Saitoh Y. et al., "Motor Cortex Stimulation for Central and peripheral Deafferentation Pain," *J Neurosurg* 92: 150-155, 2000.

Sol JC. et al., "Chronic Motor Cortex Stimulation for Phantom Limb Pain: Correlations Between pain Relief and Functional Imaging Studies," *Stereotact Funct Neurosurg* 77: 172-176, 2001.

Katayama Y. et al., "Motor Cortex Stimulation for Phantm Limb Pain: A Comprehensive Therapy with Spinal-Cord and Thalamic Stimulation," *Stereotact Funct Neurosurg* 77: 159-161, 2001.

Migita K. et al., "Transcranial Magnetic Coil Stimulation in Patients with Central Pain. Technique and Application," *Neurosurgery* 36: 1037-1040, 1995.

Garcia-Larrea L. et al., "Electrical Stimulation of Motor Cortex for Pain Control: A Combined PET-scan and Electrophysiological Study," *Pain* 83: 259-273, 1999.

Carrol D. et al., "Motor Cortex Stimulation for Chronic Neuropathic Pain: A Preliminary Study of 10 Cases," *Pain* 84: 431-437, 2000.

Pirotte B. et al., "The Zeiss-MKM System for Frameless Image-guided Approach in Epidural Motor Cortex Stimulation for Central Neuropathic Pain," *Neurosurg Focus* 11: article 3, 2001.

Mogilner AY. et al., "Epidural Motor Cortex Stimulation with Functional Imaging Guidance," *Neurosurg Focus* 11: article 4, 2001.

Saitoh Y. et al., "Motor cortex Stimulation for Deafferrentation Pain," *Neurosurg Focus* 11: article 1, 2001.

Roux FE. et al., "Methodological and Technical Issues for Integrating Functional Magnetic Resonance Imaging Data in a Neuronavigation System," *Neurosurgery* 49: 1145-1157, 2001.

Rainov N.G., "Epidural Electrical Stimulation of the Motor Cortex in Patients with Facial Neuralgia," *Clinical Neurology and Neurosurgery* 99: 205-209, 1997.

Lefaucheur JP. et al., "Pain Relief Induced by Repetitive Transcranial Magnetic Stimulation of Precentral Cortex," *Neuroreport* 12(13): 2963-2965, Sep. 17, 2001.

Nguyen JP. et al., "Motor Cortex Stimulation in the Treatment of Central and Neuropathic Pain," *Arch Med Res*. 31(3): 263-265, May-Jun. 2000.

Bezard et al., "Cortical Stimulation and Epileptic Seizure: A Study of the Potential Risk in Primates," *Neurosurgery* 45(2): 346-350, Aug. 1999.

Rezai, et al., "Neurostimulation Systems for Deep Brain Stimulation: In Vitro Evaluation of Magnetic Resonance Imaging-Related Heating at 1/5 Tesla," *Journal of Magnetic Resonance Imaging* 15: 241-250 (2002).

* cited by examiner

IMPLANTABLE CORTICAL NEURAL LEAD AND METHOD

FIELD OF THE INVENTION

This invention relates generally to implantable chronic medical electrical leads and methods of use, and more particularly to an implantable neural lead for chronic stimulation of the cerebral cortex of the brain and method of use.

BACKGROUND OF THE INVENTION

Stimulation of the motor cortex is currently a promising therapy to treat deafferentation pain syndromes, including but not limited to central deafferentation pain arising from stroke, infection, trauma, spinal cord injury, multiple sclerosis, and peripheral pain syndromes including but not limited to trigeminal neuralgia, atypical facial pain, pain arising from peripheral nerve injury or disease including but not limited to nerve plexus avulsion, phantom limb pain, etc. Furthermore, stimulation of the motor cortex or other areas of the cerebral cortex of the brain are potentially promising therapies for treatment of other neurological disorders including, but not limited to movement disorders, neurodegenerative disorders, psychological disorders, and epilepsy, and other central and peripheral disorders.

To date, the best results of chronic motor cortex stimulation for pain have been obtained when stimulation was applied precisely to the zone of motor cortex corresponding to the part of the body in which the pain is experienced. It is therefore essential to respect the somatotopic organization of the motor cortex. The combination of imaging techniques including but not limited to Computerized Axial Tomography (CAT) scans, Magnetic Resonance Imaging (MRI), and three-dimensional neuronavigation procedures for anatomical localization and intraoperative anatomical and electrophysiological testing can greatly improve localization of the zone to be stimulated, thereby improving the clinical results. The objective is to ensure that at least one of the active electrodes is directly over the desired zone of stimulation.

The motor cortex is a narrow band of cortex situated in the precentral gyrus immediately anterior to the central sulcus. The Resume® lead (four electrodes arranged in linear fashion) manufactured by Medtronic, Inc., has been used for chronic stimulation of the motor cortex. If a Resume® lead is placed parallel to the central sulcus, several adjacent zones of the motor cortex can be stimulated simultaneously allowing the treatment of extensive pain, for example involving the entire hemibody. However, as the motor cortex is fairly narrow in the antero-posterior direction and follows the sometimes pronounced convolutions of the central sulcus, the electrode may be inadvertently placed anteriorly or posteriorly to the desired location. It is therefore preferred to place the Resume® lead perpendicularly to the central sulcus in order to ensure at least one of the four contacts of the electrode is directly over the motor cortex. The essential difficulty is to very precisely locate the "height" or mediolateral zone of representation of the part of the body affected by the pain. This localization requires the use of several modalities: imaging data and intra-operative somaesthetic evoked potentials (SEP), and clinical results (muscle contractions) of motor cortex stimulation. Even with these techniques, the limited coverage of this electrode makes it difficult to treat pain involving larger or more extensive regions of the body.

In addition, the method of localization and then implantation of the chronic Resume lead involved two major steps. First, the localization using the modalities mentioned above was performed including the use of a temporary grid of multiple electrodes such as those made by Ad-Tech Medical Instrument Corporation. Once the localization step is completed, the temporary grid electrodes are removed and replaced with a Resume® lead. (In some cases two Resume® leads have been implanted for chronic motor cortex stimulation.) This removal and replacement step adds a layer of complexity and risk of error to the surgical procedure because it requires very precise placement of the chronic lead following removal of the temporary multi-electrode grid used for localization. This step also increases potential short and long-term risks to the patient and extends procedure time. Moreover, financial expense is incurred by the need for both a temporary lead and a chronic or permanent lead.

The location of the paddle when stimulating the motor cortex or elsewhere on the cerebral cortex is beneath the cranium while the lead body is outside of, and must pass through, the cranium. This transition zone over the thickness of the cranium results in mechanical strain between the paddle and the lead body. This strain makes it more difficult to get and keep the entire lead paddle in contact with the tissue being stimulated, and creates risk to the integrity of the lead insulation and conductors.

BRIEF SUMMARY OF THE INVENTION

In a first embodiment, an implantable neural lead for use in electrically stimulating the cerebral cortex is provided. The neural lead includes a paddle, a lead body and a strain relief. The strain relief connects the paddle with the lead body and offsets the lead body from the paddle to accommodate the thickness of the patient's cranium.

In a second embodiment, an implantable neural lead for use in stimulating the cerebral cortex of the brain is provided. This embodiment lead includes a lead body and a paddle. The paddle has a two-dimensional electrode array with two sets of electrodes. The first set of electrodes of at least three is in a line defining an axis of the paddle. The second set of electrodes are offset in opposite directions from the axis of the paddle.

In a third embodiment, an implantable neural lead for use in electrically stimulating the cerebral cortex is provided. This embodiment neural lead includes a lead body and a lead paddle. The paddle includes a two-dimensional array of electrodes. The paddle lead also includes a peripheral edge that defines at least two peninsulas and at least two bays.

In a fourth embodiment, a method of treating a neurological disorder by electrical stimulation of the cerebral cortex is provided. The method includes providing an implantable neural lead, creating an opening through skull bone to access an area adjacent the cortex, placing the lead paddle within the area, determining a satisfactory orientation for the lead paddle, permanently attaching the lead paddle within the area for chronic stimulation, and implanting a pulse generator in electrical communication with the lead.

In a fifth embodiment, a method of treating a neurological disorder by electrical stimulation of the cerebral cortex is provided. This embodiment method includes providing an implantable neural lead, creating an opening in the skull bone to access an area adjacent the cortex, placing the lead paddle within the area, determining whether stimulation with the first set of electrodes provides sufficient relief, based on the previous step implanting either a single or a dual channel stimulator.

DETAILED DESCRIPTION OF EXEMPLARY EMBODIMENTS

Figure 1:
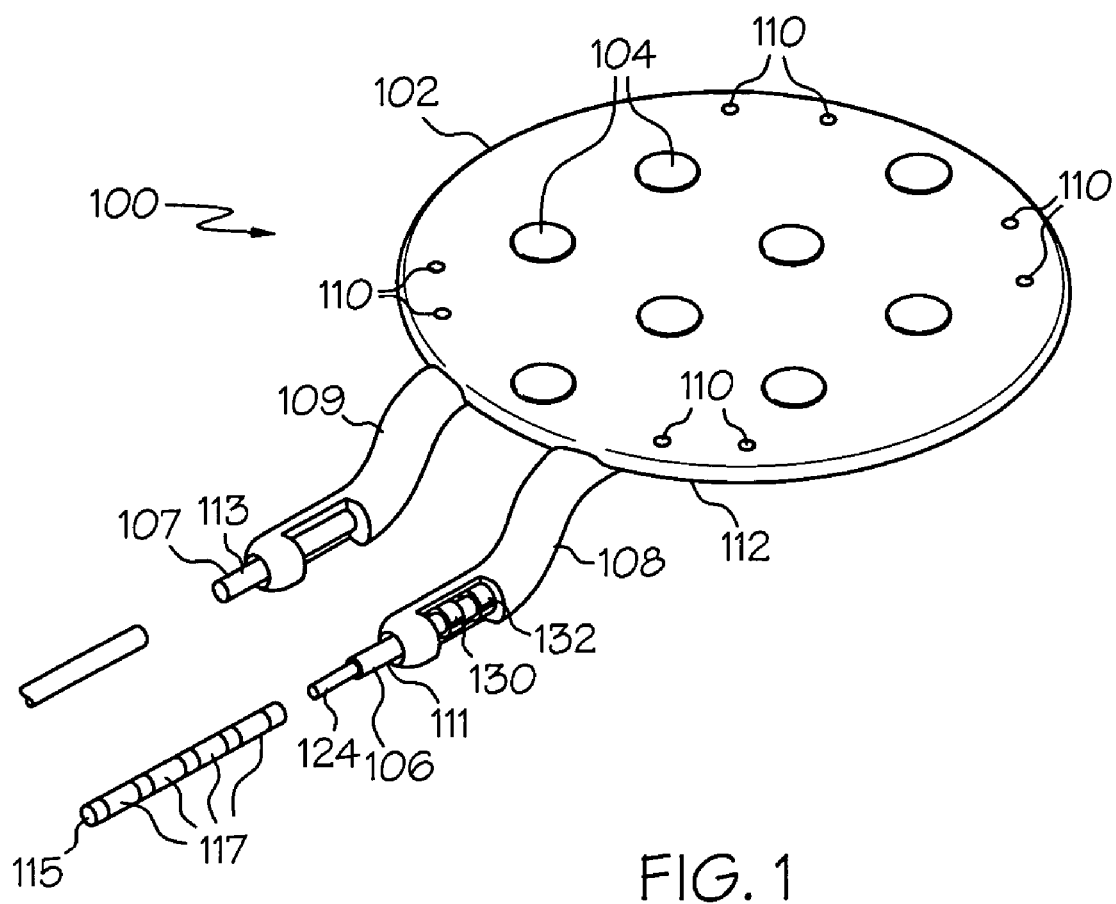
FIG. 1 shows a perspective view of one embodiment lead of the present invention including an 8-electrode array, two strain reliefs, two lead bodies and a circular paddle shape.

Referring to FIG. 1, an exemplary embodiment of an implantable neural lead of the present invention is shown. The neural lead 100 is adapted for electrically stimulating the brain. Neural lead 100 includes a paddle 102, a plurality of electrodes 104 and a lead body 106 connected to the paddle by a strain relief 108. The embodiment of neural lead 100 shown in FIG. 1 includes a second lead body 107 and a second strain relief 109 for carrying a separate channel of conducting wires. Strain reliefs 108 and 109 are shown in FIG. 1 with a partial cutaway. The neural lead 100 also includes suture holes 110 for attaching the neural lead 100 to the dura mater or other suitable tissue depending on the application.

Neural lead 100 may be used to treat any neurological disorder for which stimulation of the cortex of the brain has therapeutic value. Some example neurological disorders for use of the neural lead of this invention include, but are not limited to, treatment of pain such as facial, neck, limbic or other pain, movement disorders such as Parkinson's disease, essential tremor and dystonia, psychological disorders such as depression and obsessive compulsive disorder (OCD), epilepsy, Huntington's Disease, and neurodegenerative disorders. It is noted that pain is considered a neurological disorder for purposes of this application.

Neural lead 100 may be placed epidurally (outside the dura mater) or subdurally (beneath the dura mater). For example, in the case of treatment of pain the lead is likely to be used epidurally. In the case of epilepsy it is more likely that the lead would be used subdurally. In either case a craniotomy is performed and the paddle 102 placed beneath the cranium. In one application, lead 100 is placed epidurally adjacent the central sulcus of the cortex for stimulation to treat pain such as facial, neck or limbic pain.

Strain Relief

One of the novel features of the neural lead of the present invention is a strain relief. For purposes of this application, a strain relief is defined as a section of a lead that exists between a lead body or extension and a paddle and that displaces the lead body or extension some distance or offset from the paddle to accommodate generally the thickness of a patient's cranium. The strain relief allows the lead body or extension to lie above the cranium and the paddle to be situated beneath the cranium while reducing the amount of strain or pull between the paddle and the lead body or extension because of the displacement between the paddle and the lead body or extension.

Figure 2:
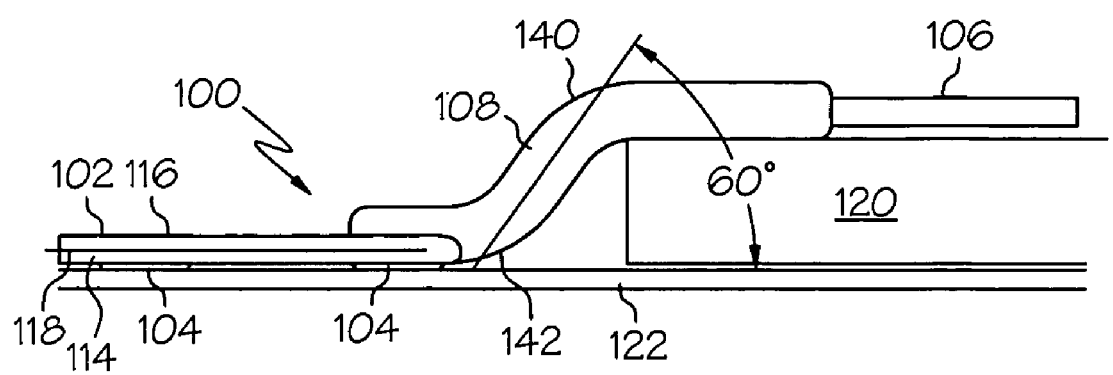
FIG. 2 shows a side view of the embodiment lead shown in FIG. 1 including one embodiment position of the lead relative to the cranium and dura mater.
Figure 3:
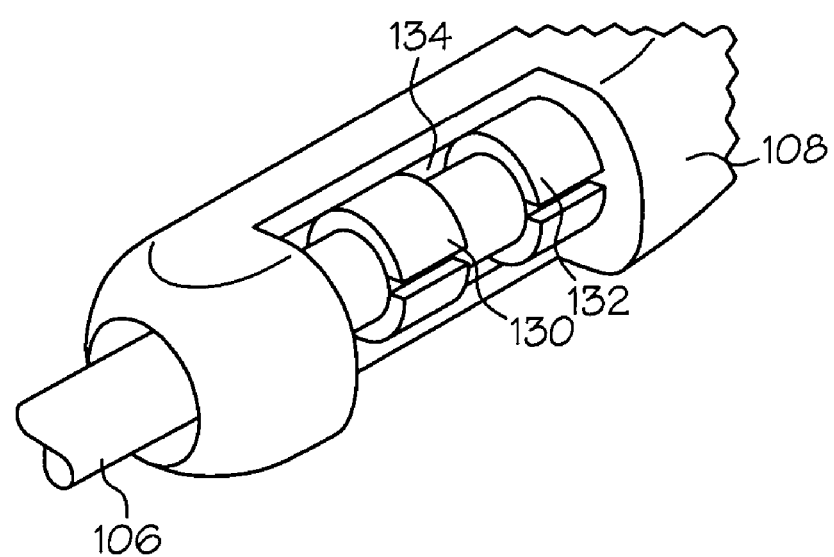
FIG. 3 shows a cutaway perspective view of one embodiment strain relief and lead body.

One embodiment strain relief 108 is shown in FIGS. 1–3. Note that the discussion and description of strain relief 108 and lead body 106 also apply to strain relief 109 and lead body 107. The strain relief 108 assists in reducing strain or pull between the paddle 102 and the lead body 106. Strain relief 108 is flexible but is sufficiently resilient resulting in shape memory to maintain an offset between the plane of the paddle 102 and the lead body 106. The purpose of the offset in the strain relief 108 is to allow a transition from the lead body 106 lying on top of the cranium 120 and the lead paddle 102 lying parallel to the lead body 106 but offset beneath the cranium 120.

As shown in FIG. 2, strain relief 108 includes two maintained bends 140 and 142. A maintained bend is bend in the strain relief that has shape memory so that if it is pressed on and deformed and then released it will return substantially to its original shape.

In the embodiment shown, the strain relief 108 is attached to the lead paddle 102 along the peripheral edge 112 of the paddle 102. The distal ends 111, 113 of the lead bodies 106, 107 are attached to the strain reliefs 108, 109 respectively.

As shown in FIG. 2, an exemplary angle between the plane of the paddle 102 and a line drawn through the middle of the strain relief 108 is 60 degrees. Preferably this angle is between 10 and 90 degrees. More preferably, this angle is between 30 and 80 degrees.

FIG. 1 also shows the proximal end 115 of lead body 106. The proximal contacts 117 are welded to the BSW wire that passes through the lead body 106 in electrical communication with the electrodes 104. Epoxy is then backfilled to bond the stripped BSW wire to the inside of the proximal contacts 117. A urethane strut 124 as described in U.S. Pat. No. 5,935,159 owned by Medtronic, Inc. may be used to prevent kinking of the lead bodies 106, 107.

FIG. 2 is a cross sectional view of the lead 100 including one embodiment interaction of the lead 100 with the patient's cranium 120 and dura mater 122. FIG. 2 shows the cross section after a craniotomy has been performed. In this embodiment of FIG. 2, the paddle 102 is placed epidurally with electrodes 104 in contact with the dura mater.

As shown in FIG. 2, the paddle 102 includes a first major surface 114 and a second opposite major surface 116 with a fibrous reinforcing layer 118 sandwiched between. The fibrous reinforcing layer helps resist stretching of the paddle 102. This additional stiffness may or may not be desired depending on the application of the lead. One embodiment of the fibrous reinforcing layer 118 is a Dacron® reinforcing mesh. The electrodes 104 extend through windows in the first major surface 114 to allow contact with the tissue to be stimulated.

Preferably, the strain reliefs 108, 109 offset the lead bodies 106, 107 from the first major surface 114 by a distance of between about 4 mm and 10 mm. More preferably, the offset is about 6 mm.

A rongeur may be used to make notches (not shown) in either the bone flap or the cranium to accommodate the strain reliefs 108, 109 when there is misalignment between the craniotomy and the stimulation site. The gap between the strain reliefs 108, 109 and the notches will eventually fill with new bone isolating all but the portion of each strain relief that lies on the cranium from any flexing due to lead body movement. The physician will position the notches such that they direct the strain reliefs 108 and 109 and the lead bodies 106 and 107 toward the location of the eventual tunnel for the extension. In an alternative embodiment, the strain reliefs or lead bodies may also be anchored or sutured outside the cranium for further reduction of flexing.

FIG. 3 provides a cutaway view of strain relief 108 to show one embodiment assembly technique. This technique involves the use of a urethane adhesive to attach two slit urethane tubes 130 and 132 to the urethane lead body 106. This assembly is inserted into the cavity 134 provided in the molded silicone rubber strain relief 108. Then the cavity 134 is filled with silicone adhesive to bond to the strain relief 108. When the adhesive has cured, it provides a mechanical lock around the tubes 130 and 132 on the lead body 106.

Figure 7:
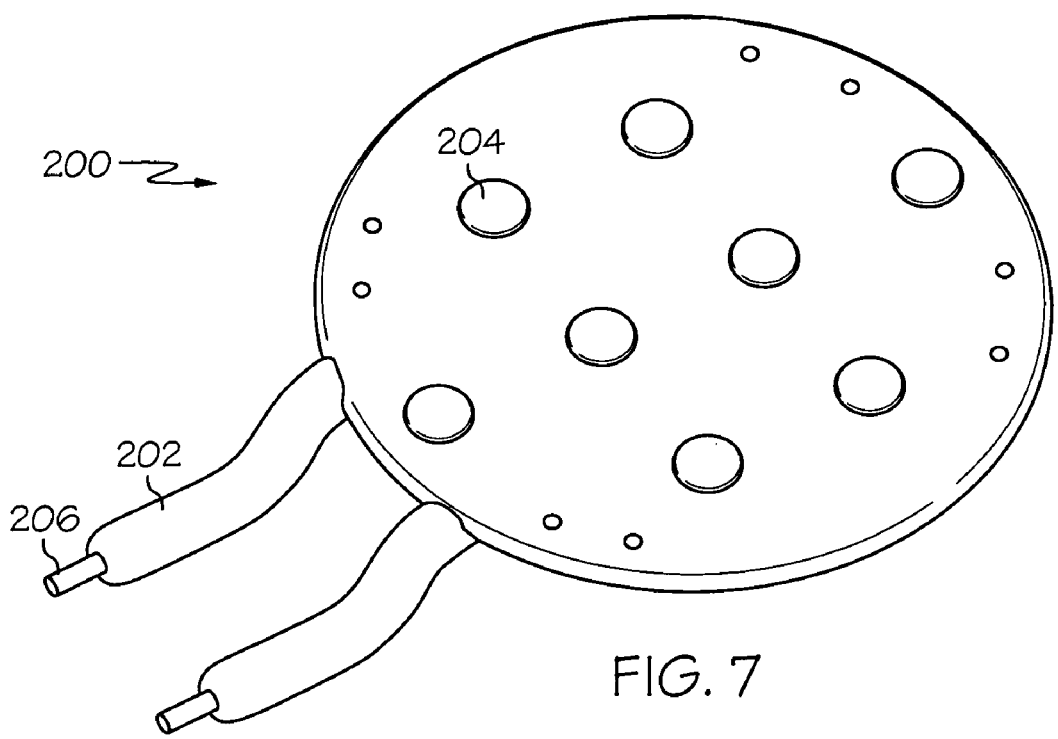
FIG. 7 shows a perspective view of an alternative embodiment lead having a strain relief connector.

The definition of a strain relief can include a strain relief connector. A strain relief connector is defined as a strain relief that includes a connector. The connector could be a female or male or any other type of connector for connecting a paddle to an extension. FIG. 7 shows a perspective view of a lead 200 that includes one embodiment strain relief connector 202 having a male connector 206. Connector 206 connects to a female connector on an extension. This embodiment lead also has 8 electrodes 204.

It is noted that the strain relief of this invention could be used with any type of paddle lead including one or two-dimensional paddle leads. A one-dimensional paddle lead is defined for this application as being a paddle lead that has a plurality of electrodes in a line and no electrodes out of alignment with the line. A two-dimensional paddle lead is defined for this application as being a paddle lead with three or more electrodes positioned in such a way that they are not all in a line. A two-dimensional paddle lead includes a lead with a line of electrodes and one electrode out of alignment with the line. For purposes of this application, a two-dimensional paddle lead also includes non-planar orientation of electrodes.

An alternate embodiment lead of the present invention could include only a single lead body and single strain relief. In such an embodiment, all of the conducting wires would pass through the single lead body and strain relief instead of being separated as shown in FIG. 1. Furthermore, more than two lead bodies and more than two strain reliefs could be utilized.

Electrode Configuration

Figure 5:
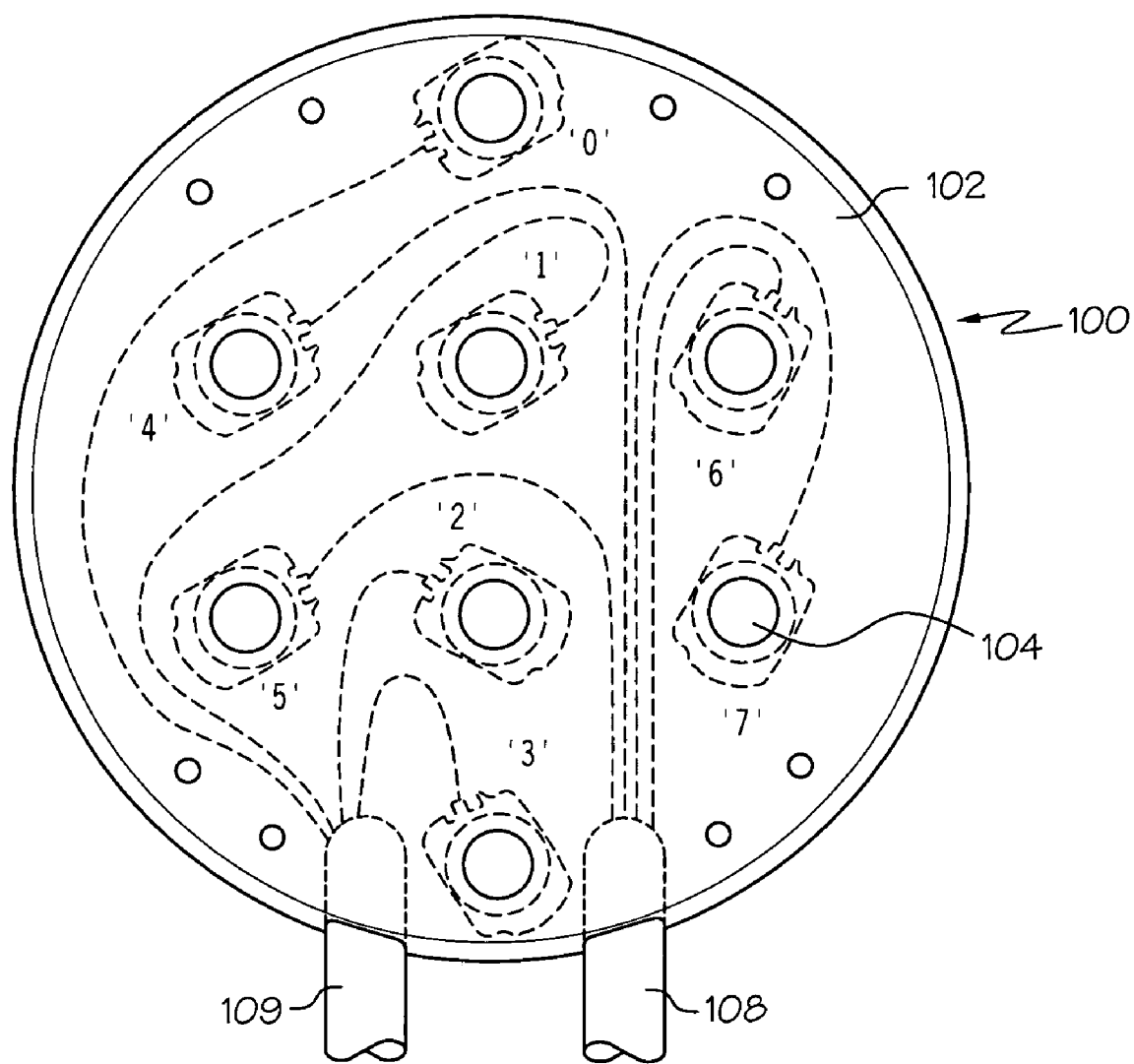
FIG. 5 shows a view of the embodiment lead shown in FIG. 1 as viewed from the side opposite the exposed electrodes.

The number of electrodes 104 as well as the position of the electrodes 104 on the paddle 102 may vary greatly within the scope of the present invention. In one particularly advantageous embodiment, the lead paddle 102 has a two dimensionally distributed electrode array including a plurality of electrically isolated electrodes, the plurality of electrodes including a first set of at least three electrodes defining an axis of the paddle and a second set of electrodes offset in opposite directions from the axis of the paddle. For example, the first set of electrodes in FIG. 5 is marked as electrodes 0, 1, 2, and 3 defining an axis of the paddle 102. The second set of electrodes is electrodes 4, 5, 6, and 7 with electrodes 4 and 5 offset from the axis of the paddle 102 in an opposite direction from electrodes 6 and 7 respectively.

Other embodiments having more or fewer electrodes are considered. For example, the first set of electrodes could be only three electrodes in a line and forming an axis of the paddle with a fourth electrode offset on one side of the axis of the paddle and a fifth electrode offset on the other side of the axis of the paddle (embodiment not shown but consider FIG. 5 but without electrodes 3, 5, and 7).

The lead shown in FIG. 1 has 8 electrodes 104. This distribution of electrodes allows stimulation parallel to the central sulcus while ensuring stimulation of the motor cortex. The electrode configuration shown on FIG. 1 allows for the certainty of stimulating parallel to the central sulcus and ensuring stimulation of the motor cortex.

Figure 9:
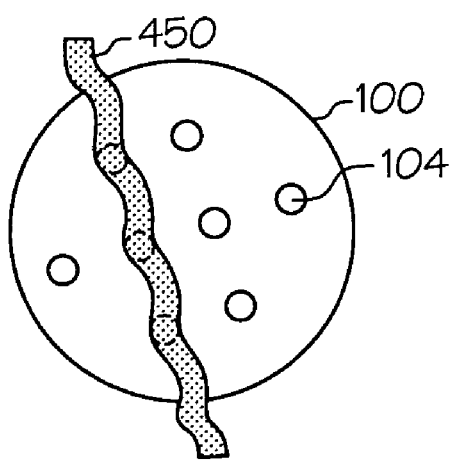
FIG. 9 shows one embodiment placement of the lead of FIG. 1 relative to the central sulcus.
Figure 10:
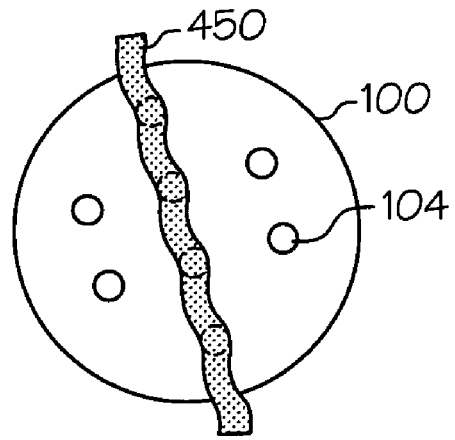
FIG. 10 shows another embodiment placement of the lead of FIG. 1 relative to the central sulcus.

FIGS. 9 and 10 illustrate two exemplary orientations or placements of the lead 100 relative to the central sulcus 450. As can be seen and envisioned there are many possible placements of the lead 100 relative to the central sulcus or other fissure of the cortex. The exact placement desired will depend on the results of the navigational and other screening and positioning techniques performed.

Figure 4:
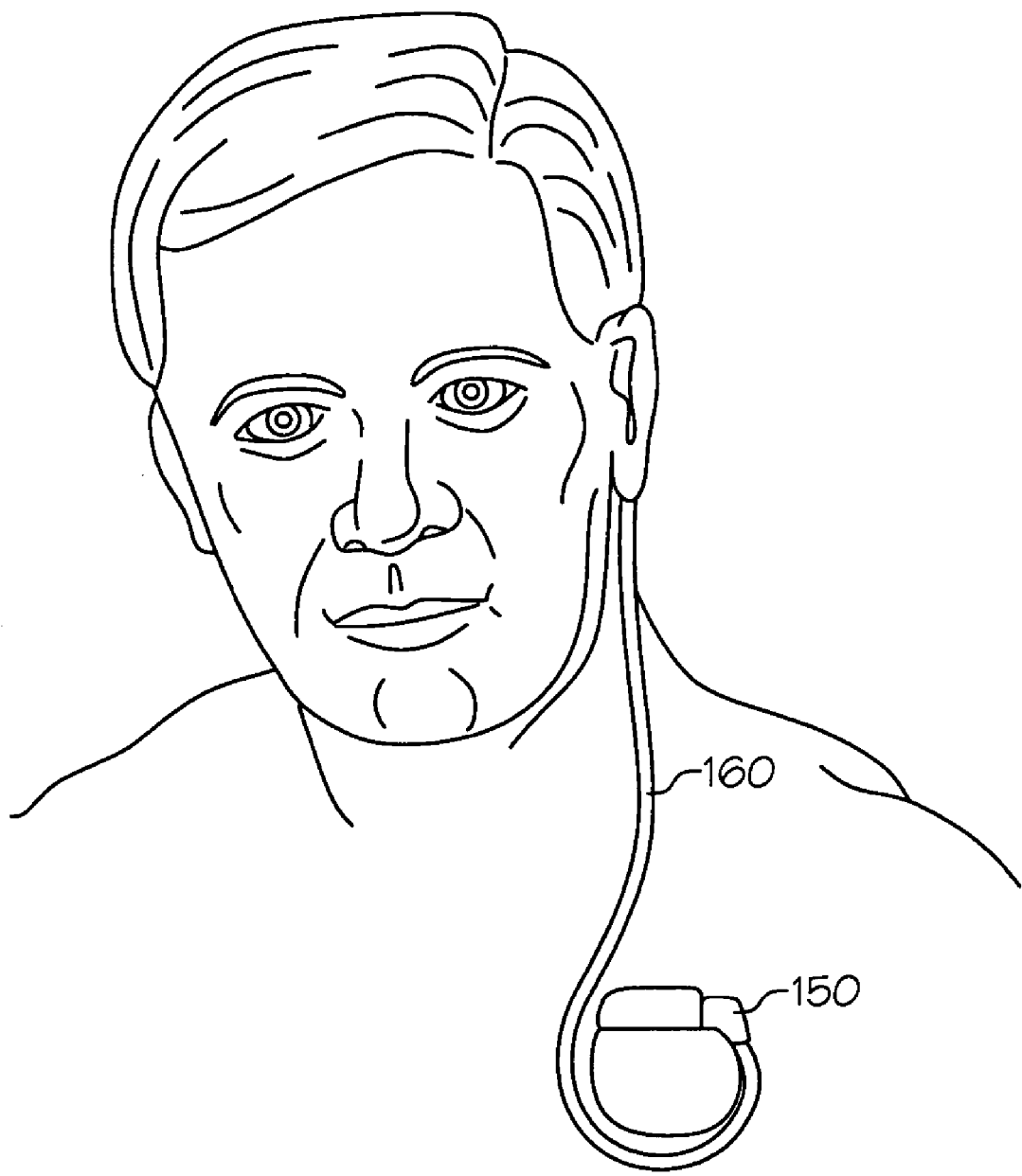
FIG. 4 shows a front view of a patient with a stimulator connected to an extension that connects to the lead body.

The neural lead of this invention may be used with any pulse generator. FIG. 4 shows a pulse generator 150 implanted pectorally and connected to an extension 160 that is connected to a lead 100 (not shown in FIG. 4). In a preferred embodiment, the lead 100, 200 or 300 is used with a Synergy® or Soletra® implantable pulse generator (IPG) made by Medtronic, Inc. The Synergy® IPG is capable of dual channel stimulation so that each set of electrodes is a separate channel. The Synergy® stimulator is also capable of stimulating across channels which is helpful in some cases of motor cortex stimulation.

In the embodiment shown in FIG. 5, the conductive wires from electrodes 0, 1, 2, and 3 are carried through strain relief 109 and lead body 107. The wires from electrodes 4, 5, 6, and 7 are carried through strain relief 108 and lead body 106. In this way each lead body and hence each set of electrodes can be connected to a separate channel of a dual channel stimulator.

Paddle Dimensions

Figure 6:
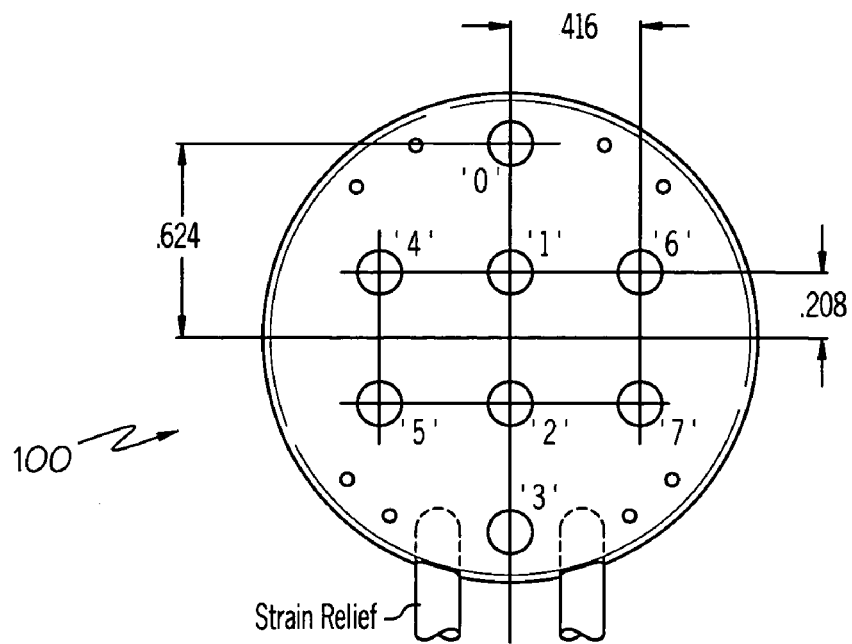
FIG. 6 shows the same view as FIG. 5 without showing the conductive wires but showing dimensions.

In a preferred embodiment, the diameter and thickness of the paddle are 1.575 inches and 0.054 inches, respectively. Other preferred dimensions are shown in FIG. 6 that shows the lead paddle 102 from the side opposite the exposed electrodes 104 (the side facing toward the cranium facing away from the brain). FIG. 6 also shows one way of assigning numbers to the electrodes. The lead 100 may be marked with these numbers for use by the physician. Of course the electrodes could be numbered or otherwise marked in any number of ways.

Paddle Shape

Figure 8:
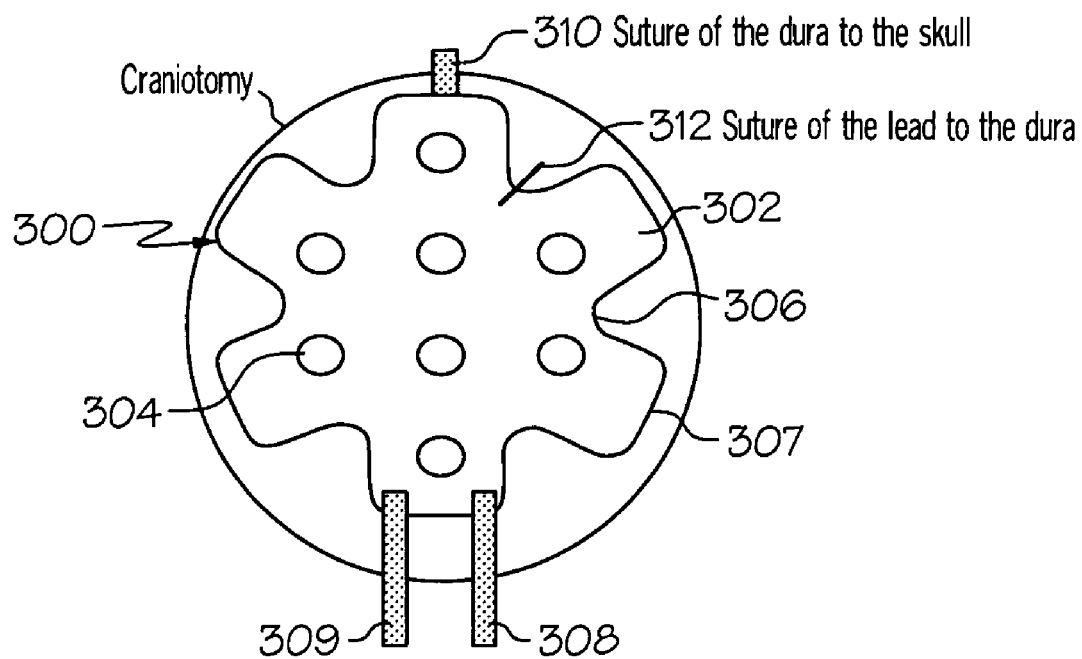
FIG. 8 shows a top view of a further alternative embodiment lead having a peripheral edge defining multiple peninsulas and bays.

The shape of the paddle may be round as shown in FIGS. 1, 5, 6, and 7 or it may be other shapes. Because craniotomies are typically round, one preferred embodiment is the round shape. However, an alternative preferred embodiment is shown in FIG. 8. This "flower" design paddle lead 300 allows the craniotomy size to be smaller and allow for the paddle to be more easily slid under the cranium around the edges of the craniotomy. The lead 300 includes paddle 302, electrodes 304, and strain reliefs 308 and 309. The paddle 302 includes a peripheral edge defining six peninsulas 307 and six bays 306, wherein the peninsulas 307 can be easily slid under the cranium. Reference numerals 310 and 312 show the location of suture of the dura to the cranium and suture of the lead to the dura respectively.

Method of Treating a Neurological Disorder

Figure 11:
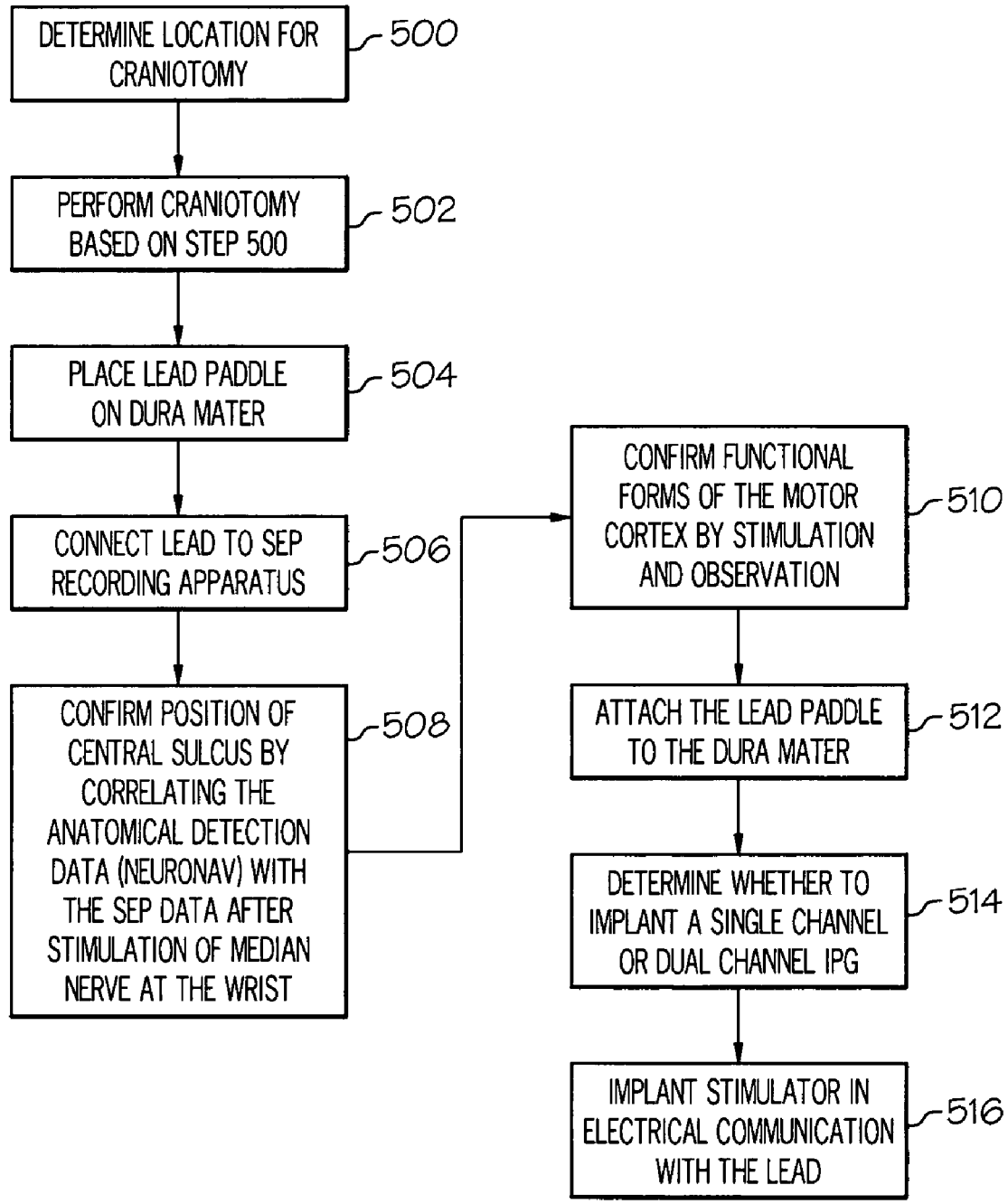
FIG. 11 is a flow chart showing one embodiment method of treatment of a neurological disorder.

Due to the distribution of the electrodes 104, the lead 100, 200 or 300 can also be used for intraoperative detection, as these 8 electrode leads can be used to record somaesthetic evoked potentials, which confirm the position of the central sulcus. Similarly, this same electrode can be used to stimulate the cortex intraoperatively in order to confirm the position of the various functional zones of the motor cortex. This technique should therefore represent a major financial economy, since a fairly costly disposable electrode with several contacts previously had to be used for electrophysiological detection, while the Resume® lead was used for chronic stimulation. Also the use of the lead of this invention for both localization and chronic stages eliminates a layer of complexity to the surgical operation reduces potential for placement error, reduces short and long-term risks to the patient, reduces procedure time, and makes the procedure more economical An exemplary embodiment method of treating a neurological disorder is shown in FIG. 11. As indicated by block 500, localization of the target zone of the cortex is performed by imaging techniques including but not limited to Computerized Axial Tomography (CAT) scans, Magnetic Resonance Imaging (MRI), and three-dimensional imaging with a neuronavigation systems and procedures.

As indicated by block 502, a circular craniotomy, 4 to 5 cm in diameter, is performed with the guidance of the neuronavigation system. The 8-electrode paddle is placed on the dura mater and connected to a somaesthetic evoked potential (SEP) recording apparatus as shown in blocks 504 and 506.

The position of the lead over the central sulcus is confirmed by correlating the anatomical detection data (neuronavigation) with the SEP data obtained after stimulation of the median nerve at the wrist as shown in block 508.

As shown in block 510, the position of the various functional zones of the motor cortex can be confirmed by stimulating the electrodes supposedly situated directly over the motor cortex and observing the response. For example, in order to treat facial pain, the zone of motor cortex for which stimulation induces muscle contractions of the face is identified.

As indicated in block 512, the lead is then attached to the dura mater by several sutures. Other attachment methods may be used such as anchors or other methods known in the art.

When anatomical and electrophysiological data are concordant and very clear, the two leads of the electrode are connected during the same operation to an IPG.

Depending on the results of the above trials and screening, the next step shown as block 514 involves a determination of whether a single channel IPG such as a Soletra® stimulator or a dual channel stimulator such as a Synergy® stimulator is preferred. If use of electrodes 0, 1, 2, and 3 are sufficient to alleviate pain or otherwise reduce symptoms of the disorder, then a single channel stimulator is sufficient. If use of the other electrodes 4, 5, 6, or 7 provides further reduction in symptoms, then a dual channel stimulator may be preferred.

As indicated in block 516, the selected stimulator is then implanted in electrical communication with the electrodes 104.

When there is a doubt about efficacy based on location or other factors, due to a discrepancy between anatomical and electrophysiological data, the leads may be exteriorized and a clinical test performed during the days following the operation. A single channel or dual channel stimulator may then be implanted depending on the clinically effective electrodes.

Thus, embodiments of the implantable cortical neural lead and method are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable neural lead adapted for use in electrically stimulating the cerebral cortex, the lead comprising:
   a paddle having first and second opposite major surfaces, and a plurality of electrically isolated electrodes exposed through the first major surface;
   a lead body including a plurality of electrically conductive wires in electrical communication with the electrodes; and
   a strain relief connecting the paddle with the lead body, the strain relief offsetting the lead body from the second surface of the paddle a distance sufficient to accommodate the thickness of a patient's skull bone wherein the strain relief comprises at least a first maintained bend.

2. The implantable neural lead of claim 1 in which the lead body has a distal end adjacent the strain relief, and wherein the strain relief further comprises a second maintained bend, and wherein the strain relief tends to hold the paddle and the distal end of the lead body in a generally parallel yet displaced relationship.

3. The implantable neural lead of claim 2 in which the paddle has a peripheral edge, the strain relief being connected to the paddle along the peripheral edge.

4. The implantable neural lead of claim 3 in which the strain relief causes the electrically conductive wires to extend along a generally "S" shaped path between the lead body and the paddle.

5. The implantable neural lead of claim 4 in which the strain relief provides means for relieving strain as tension is applied between the paddle and the lead body.

6. The implantable neural lead of claim 5 in which the strain relief is molded of elastomeric material, the electrically conductive wires each integrally extending between the electrodes and the proximal end of lead body.

7. The implantable neural lead of claim 6 in which the paddle further includes a fibrous reinforcing layer sandwiched between resiliently-flexible layers.

8. The implantable neural lead of 2 in which the strain relief offsets the lead body from the first major surface of the paddles a distance between about 4–10 mm.

9. The implantable neural lead of claim 8 in which the strain relief offsets the lead body from the first major surface of the paddle a distance of about 6 mm.

10. The implantable neural lead of claim 1 in which the plurality of electrically isolated electrodes comprises a two dimensionally distributed electrode array.

11. The implantable neural lead of claim 1 wherein the strain relief comprises a strain relief connector.

12. An implantable neural lead adapted for use in electrically stimulating the cerebral cortex, the lead comprising:

a paddle having first and second opposite major surfaces, and a plurality of electrically isolated electrodes exposed through the first major surface;

a lead body including a plurality of electrically conductive wires in electrical communication with the electrodes; and a strain relief connecting the paddle with the lead body, the strain relief offsetting the lead body from the first major surface of the paddle a distance between about 4–10 mm to accommodate the thickness of a patient's skull bone.

13. The implantable neural lead of claim 12 in which the strain relief offsets the lead body from the first major surface of the paddle a distance of about 6 mm.

14. An implantable neural lead adapted for use in electrically stimulating the cerebral cortex, the lead comprising:

a paddle having first and second opposite major surfaces, and a plurality of electrically isolated electrodes exposed through the first major surface;

a lead body including a plurality of electrically conductive wires in electrical communication with the electrodes; and a strain relief connecting the paddle with the lead body, the strain relief offsetting the lead body from the second surface of the paddle a distance sufficient to accommodate the thickness of a patient's skull bone, wherein the strain relief comprises a strain relief connector.

* * * * *